United States Patent
Pugh et al.

(10) Patent No.: US 10,117,790 B2
(45) Date of Patent: Nov. 6, 2018

(54) PERSONAL HYGIENE PRODUCT WITH A DIGITAL ELEMENT

(71) Applicant: Johnson & Johnson Vision Care, Inc., Jacksonville, FL (US)

(72) Inventors: Randall Braxton Pugh, St. Johns, FL (US); William Chester Neeley, Melbourne, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 334 days.

(21) Appl. No.: 15/045,663

(22) Filed: Feb. 17, 2016

(65) Prior Publication Data

US 2016/0250081 A1    Sep. 1, 2016

Related U.S. Application Data

(60) Provisional application No. 62/121,066, filed on Feb. 26, 2015.

(51) Int. Cl.
| | |
|---|---|
| *A61F 13/42* | (2006.01) |
| *A61F 13/84* | (2006.01) |
| *A61F 13/20* | (2006.01) |
| *G08B 21/20* | (2006.01) |
| *G08B 21/18* | (2006.01) |
| *G08B 21/24* | (2006.01) |
| *G01N 27/04* | (2006.01) |

(52) U.S. Cl.
CPC .............. *A61F 13/42* (2013.01); *A61F 13/20* (2013.01); *A61F 13/2051* (2013.01); *A61F 13/84* (2013.01); *G08B 21/182* (2013.01); *G08B 21/20* (2013.01); *G08B 21/245* (2013.01); *A61F 2013/424* (2013.01); *A61F 2013/427* (2013.01); *A61F 2013/8473* (2013.01); *A61F 2013/8479* (2013.01); *G01N 27/048* (2013.01)

(58) Field of Classification Search
CPC ........ A61F 2013/424; A61F 2013/8479; A61F 13/42
USPC .......................................................... 604/361
See application file for complete search history.

(56) References Cited

U.S. PATENT DOCUMENTS

| | | | |
|---|---|---|---|
| 4,704,108 A | * | 11/1987 | Okada ..................... A61F 13/42 604/358 |
| 4,800,370 A | | 1/1989 | Vetecnik |

(Continued)

FOREIGN PATENT DOCUMENTS

| | | |
|---|---|---|
| WO | WO199917692 | 4/1999 |
| WO | WO2008026117 A1 | 3/2008 |
| WO | WO2011043724 A1 | 4/2011 |

OTHER PUBLICATIONS

"Magnetic self-locating connectors," https://web.archive.org/web/20141031055912/http://www.rosenberger.com/en/products/medical/magnetic.php, Oct. 31, 2014.*

(Continued)

*Primary Examiner* — Susan Su
(74) *Attorney, Agent, or Firm* — Carl J. Evens

(57) ABSTRACT

A personal hygiene product with a digital element is described. In one embodiment, a conductive sensor assembly is disposed within the personal hygiene product that includes one or more moisture sensors that generate a resistive signal indicative of saturation of the personal hygiene product when in wetting contact with menstrual fluid.

19 Claims, 8 Drawing Sheets

(56) References Cited

U.S. PATENT DOCUMENTS

| | | | | |
|---|---|---|---|---|
| 5,760,694 | A * | 6/1998 | Nissim | A61F 13/42 128/885 |
| 5,904,671 | A * | 5/1999 | Navot | A61F 13/20 340/573.5 |
| 6,348,640 | B1 | 2/2002 | Navot | |
| 6,570,053 | B2 | 5/2003 | Roe | |
| 6,583,722 | B2 | 6/2003 | Jeutter | |
| 6,677,859 | B1 * | 1/2004 | Bensen | A61F 5/48 340/552 |
| 7,250,547 | B1 * | 7/2007 | Hofmeister | A61F 13/42 340/573.5 |
| 7,806,882 | B1 | 10/2010 | Larkin | |
| 8,866,624 | B2 | 10/2014 | Ales, III | |
| 9,241,840 | B2 | 1/2016 | Krim | |
| 9,291,589 | B2 | 3/2016 | Wong | |
| 9,408,757 | B2 | 8/2016 | Elfström | |
| 2002/0021220 | A1 * | 2/2002 | Dreyer | A47K 11/04 340/573.1 |
| 2004/0064114 | A1 * | 4/2004 | David | A61F 13/2051 604/361 |
| 2005/0195085 | A1 * | 9/2005 | Cretu-Petra | A61B 5/6808 340/573.5 |
| 2010/0305530 | A1 | 12/2010 | Larkin | |
| 2011/0125116 | A1 | 5/2011 | Larkin | |
| 2012/0040655 | A1 | 2/2012 | Larkin | |
| 2013/0233063 | A1 | 9/2013 | Wang | |
| 2014/0276503 | A1 * | 9/2014 | Sheldon | A61F 13/42 604/360 |
| 2014/0296808 | A1 * | 10/2014 | Curran | A61F 13/42 604/361 |
| 2015/0234372 | A1 * | 8/2015 | Slupik | G05B 15/02 700/275 |
| 2016/0045378 | A1 * | 2/2016 | Geloen | A61F 13/42 604/361 |
| 2017/0112681 | A1 | 4/2017 | Mancini | |
| 2017/0150917 | A1 | 6/2017 | Brief | |

OTHER PUBLICATIONS

European Search Report dated Jul. 16, 2016 for corresponding EP Appln. No. 16157454.6.
Du, Winncy Y. *Resistive, capacitive, inductive, and magnetic sensor technologies*, Dec. 9, 2014, pp. 26-27 fig. 2.2.
Search Report for Corresponding SG Appln. No. 10201601386V dated May 11, 2018.

* cited by examiner

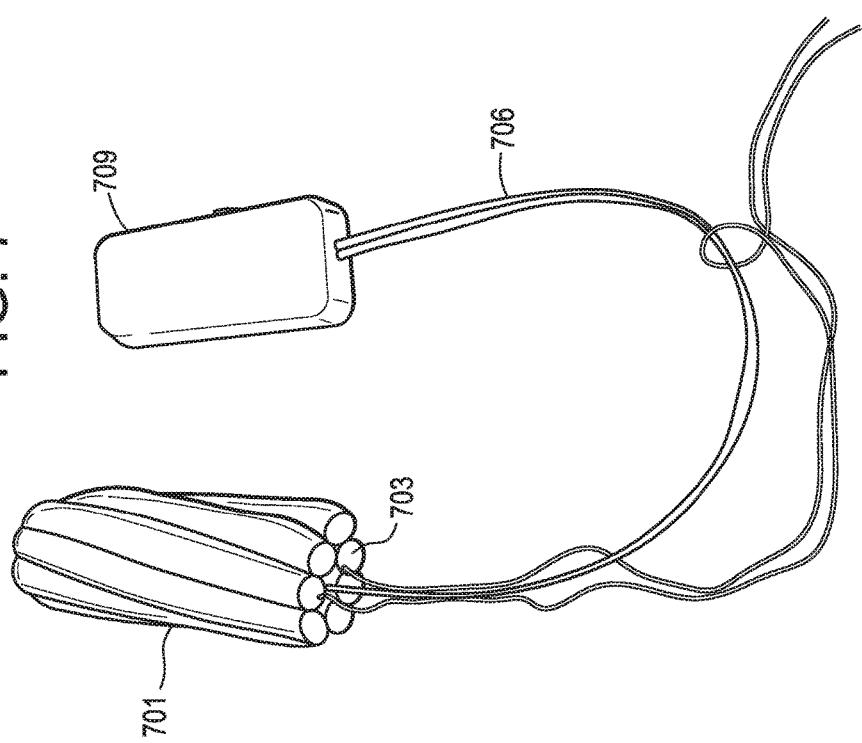

PERSONAL HYGIENE PRODUCT WITH A DIGITAL ELEMENT

This application claims the benefit of U.S. Provisional Application Ser. No. 62/121,066, filed Feb. 26, 2015, which is hereby incorporated by reference.

BACKGROUND OF THE INVENTION

1. Field of the Invention

This relates to personal hygiene products used for personal care, primarily for absorption or containment of bodily fluid, and more particularly, to a personal hygiene product with a digital element that may be utilized to sense and wirelessly communicate discharge related data to the user via a smart hand held electronic device.

2. Discussion of the Related Art

The basic structure of a personal hygiene product has not varied greatly over time. The needs of users have also not varied: to prevent seepage onto the skin, clothing, or external environment through maximized absorption and predictability of the personal hygiene product's absorption capacity. Personal hygiene products include tampons; bed pads; disposable adult diapers; disposable adult briefs; disposable sanitary napkins, sanitary napkins with adhesive strips and wings; and panty liners. Most people will at some point in their life use a personal hygiene product for a period of time. Personal hygiene products historically involve a one-size-fits-all approach.

A woman, for example will use an estimated average of 10,000 personal hygiene products in a lifetime. Even though feminine hygiene products come in different sizes and shapes designed for varying absorbent capacity, no product is 100 percent effective in preventing spills or leakage because variance in menstruation may lead to oversaturation. Each woman's menstrual flow varies over the course of her menstruation, with some days being lighter or heavier than others. Because of menstrual variance, accidents or overflows may occur where the personal hygiene product becomes oversaturated and spills outside of the absorbent area. Continued use of an oversaturated hygiene product may lead to negative health impacts such as bacterial infections or toxic shock syndrome.

Many women manually track or monitor their menstrual cycle for predictability to avoid the unexpected start of menstruation in the absence of a personal hygiene product or accidents of the sort discussed above. There are over two hundred smart device applications available to monitor menstruation manually. Users enter data into the application on a smart device, for example a smart phone or other hand held device, and the application generates data predicting, for example, menstrual start day, flow pattern, and length of menstruation. Many of these smart device applications issue alerts when menstruation is expected to start and end. All available devices, however, rely on data based on the subjective and manual entry of the user and may not reliably meet the primary needs most female hygiene product users have: predictability and reliability. None of these applications are able to actively monitor the active absorption capacity of a personal hygiene product while a user is wearing or using it.

Personal hygiene products are also used, for example, by the elderly, injured, persons with disability, and persons with incontinence. Personal hygiene products may be used in a variety of settings: community, home, hospital, and nursing homes. In particular, hospitals and nursing home staff have limited resources to constantly monitor patients or residents who wear a personal hygiene product. The result is that patients and residents risk prolonged wear of a hygiene product that may result in sores or infection. Additionally, most hospitals and nursing homes are equipped with a lift team or machine to facilitate changing a personal hygiene product for a person who is not mobile. However, there may only be one lift team or machine per facility. As a result, a staff person changing a personal hygiene product alone risks injury on the job. The nursing and personal caretaker professions have the highest rates of injury resulting from on-the-job lifting because of individually lifting and maneuvering a patient's or resident's body to change a personal hygiene product during the course of periodic checks during their shift.

Current efforts to monitor personal hygiene products in the settings above rely on periodic check and patient report. There is a need for hospitals and nursing homes to have real-time data and information in order to more efficiently respond to, for example, a personal hygiene product change, with adequate resources. Such a response will reduce injury and increase health safety for both the patient/resident and staff.

In addition to the need for predictability and reliability in use of a personal hygiene product, a personal hygiene product is situated either proximate to or inserted into the body and as a result is able to collect data about patterns of discharge and biometrics in a way that a manual-entry application is unable to capture. This data is beneficial, to avoid social embarrassment, and also for a user's overall health, for example, to provide accurate data to a physician or to alert the user if there are disruptions in normal patterns of bodily fluid discharge.

For example, menstrual issues and patterns of discharge are one of the most common reasons for a woman to see a doctor. Generally, a doctor's first response will be for the woman to keep a "menstrual diary" as a record of the period dates, length of periods, flow, etc. Menstruation that departs from a normal monthly cycle, such as lasting longer or shorter than usual or not occurring at all, may indicate an underlying health issue. For example, abnormally long menstrual bleeding may indicate irregularities such as polyps, fibroids, cancer or infection within the uterus or cervix. A number of conditions may be revealed from menstrual flow data: dysmenorrhea (painful periods); oligomennorhoea (irregular periods); amenorrhea (lack of periods); and menorrhagia (heavy periods).

The location of a personal hygiene product is able to gather internal and external biometric data such as temperature or pH. Menstruation, for example, also includes discharge with biometric information. The process of monthly menstruation involves process in which uterus sheds the endometrium to allow a new lining to replace it. Menstrual fluid is comprised of a uterine blood, meaning the endometrial tissue, vaginal secretions, and cervical fluids. Menstrual fluid also includes information such as hormones such as estrogen and progesterone and enzymes related to pregnancy such as hydrolytic enzymes and lysosomes.

In the home health setting, for example, individuals receive periodic check-ups by home health staff ranging from multiple times daily to weekly. Isolated visits may not capture or accurately give warning if an individual has additional health issues if those issues do not present during a check-up. The valuable biometrics that may be gleamed from a personal hygiene product would accurately convey extensive data that if available electronically to a health professional would provide a more accurate and holistic understanding of the patient's health. Additionally, a personal hygiene product with a digital element may facilitate remote monitoring either by a health care professional or family member.

The proper combination of a personal hygiene product incorporated with a digital element capable of interfacing with a smart hand held electronic device would meet the ultimate needs of personal hygiene product consumers. The digital element needs to biocompatible and comprised of an array capable of wireless communication. Accordingly, there exists a need for providing a personal hygiene product capable of gathering, processing, and communicating data about the product's absorbent capacity and individual user's bodily fluid discharge to smart hand held electronic device of a user. There are also exists a need for an individual user to be able to interface with the data once communicated to the smart hand held electronic device.

SUMMARY OF THE INVENTION

A personal hygiene product with a digital element in accordance with the present invention overcomes the limitations with the prior art as briefly discussed above.

The present invention describes a device comprising a personal hygiene product with a digital element. In some embodiments, the personal hygiene product with a digital element comprises a digital element located on the exterior of a personal hygiene product that comes into direct contact with body fluid. In some embodiments, the personal hygiene product with a digital element comprises a digital element that is embedded within the absorbent core of a personal hygiene product. In some embodiments, the personal hygiene product with a digital element comprises a personal hygiene product with digital capabilities that connects to an external digital element.

In some embodiments, the personal hygiene product may be a feminine hygiene product used for menstruation or discharges of other bodily fluids. In some embodiments, the hygiene product may be a diaper, pad, or material used by adults to absorb or contain the discharge of bodily fluids.

In some embodiments, a conductive sensor assembly is disposed within a core of the personal hygiene product. The conductor sensor assembly may include a sensor array including one or more moisture sensors. Each moisture sensor may include a moisture sensitive switch coupled to a resistor where the resistance value of the moisture sensitive switch is less than the resistance value of the resistor.

In some embodiments, the digital element of the personal hygiene product may comprise a sensor array within the absorbent core of the hygiene product that magnetically connects to an external digital element. The digital element may comprise a battery, communication circuit, and sensor array.

In accordance with one aspect, the digital element may comprise a circuit board and battery power source.

In some embodiments, the digital element located on or within the personal hygiene product may comprise a sensor array and electrical components disposed on a substrate encapsulated by a biocompatible material. In some embodiments, the digital element may be printed onto the personal hygiene product and comprise a sensor array and electrical components located on a substrate.

In some embodiments, the digital element located on or within the personal hygiene device may comprise a sensor array, electrical components, and wireless communication device located on a substrate encapsulated by a biocompatible material.

In some embodiments, the sensor array may send data or information to the wireless communication device via a processor in the electrical components.

In some embodiments, the wireless communication device may communicate with a smart hand electronic held device.

The digital element may be integrated into or embedded within the hygiene product and generate output information through a communication system with the ability to interface with a smart hand held electronic device.

A person may use one hygiene product with a digital element that communicates wirelessly with a smart hand held electronic device. A person may also use two hygiene products simultaneously where the digital element in one hygiene product communicates with a communication system in a second hygiene product that communicates with a smart hand held electronic device. The digital element may be activated by some physical step, for example, connecting the conductive ribbon to the external digital element, unfolding a pad or pushing a tampon through the applicator.

In accordance with some embodiments, the digital element may comprise a sensor system including a sensor array to detect fluid levels in the product. The sensor system may also include a system controller configured to sample each sensor array to calculate liquid levels and provide an output control signal, and at least one actuator configured to receive the output control signal.

In accordance with one aspect, the digital element may comprise a sensor system including a transverse or longitudinal pair of sensors to detect fluid levels in the product. The sensor system may also include a system controller configured to sample each sensor array to calculate liquid levels and provide an output control signal, and at least one actuator configured to receive the output control signal.

In accordance with another aspect, the digital element may comprise a sensor system including a sensor array capable of detecting biometrics, for example, pH level and temperature, and provide an output control signal, and at least one actuator configured to receive the output control signal.

In accordance with another aspect, the digital element may comprise a sensor system including a sensor array capable of detecting biometrics, for example, hormonal levels, and provide an output control signal and at least one actuator configured to receive the output control signal.

The present invention relates to a hygiene product that incorporates a digital element capable of interface with a smart hand held electronic device, for example, a smartphone. In accordance with one aspect, the electronic device may gather data received from each use of a hygiene product with a digital element or combination of hygiene products with digital elements.

In accordance with one aspect, the electronic device may comprise an event notification mechanism that may notify the user of an event that may occur, for example within the hygiene product or an alert related to a biometric change. In accordance with another aspect, the electronic device may analyze and aggregate the data communicated from the digital element in the hygiene product to generate a report, summary, chart, or visual tool for the user, for example, reflecting menstrual flow patterns. The electronic device may provide a link for purchase options of hygiene products based on data, for example, a home health program ordering weekly hygiene products for delivery to the user in the home.

In accordance with one aspect, the application or software may receive data from the digital element on the level of saturation of the hygiene product and absorbent capacity of the product while the user is wearing it. The application or software may signal the user through a warning or alert if and/or when maximum saturation will occur so the user can change the hygiene product prior to leakage or spillage.

In accordance with one aspect, the application or software may use data gathered from each use of a hygiene product with a digital element to generate predictive analytics to advise the user of information related to the flow or discharge. Such an embodiment may, for example, provide a woman information about her menstrual cycle such as her estimated start day and time of day. Such an embodiment may also, for example, provide a woman information on what hygiene product level of absorbency is recommended for a given day in her menstrual cycle.

In accordance with one aspect, the electronic device may receive data from the digital element that convey personal health information such as body temperature for fertility monitoring or biometrics to indicate infection. Such an embodiment may, for example, allow a user to present data aggregated by the external electronic device to a primary care physician.

In accordance with another aspect, the application or software may use data gathered from the use of a hygiene product with a digital element to alert and/or mobilize facility resources to change the hygiene product. Such an embodiment, for example, may alert a nursing station and then a lifting team, that a hygiene product needs changing. Such an embodiment, for example, may also allow a facility to more accurately identify resources needed to best protect the health of patients, residents, or staff.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 7 shows a personal hygiene product coupled to a digital element in accordance with an embodiment of the invention.

DETAILED DESCRIPTION OF THE PREFERRED EMBODIMENTS

A device comprising a hygiene product with a digital element capable of interface with a smart hand held electronic device is disclosed in this application. In the following sections, detailed descriptions of various embodiments are described. The descriptions of various embodiments are illustrative embodiments, and various modifications and alterations may be apparent to those skilled in the art. Therefore, the exemplary embodiments do not limit the scope of this application. The digital element is designed for use in or adjacent to the body of a living organism.

Glossary

In the description and claims below, various terms may be used for which the following definitions will apply:

"Biocompatible" as used herein refers to a material or device that performs with an appropriate host response in a specific application. For example, a biocompatible device does not have toxic or injurious effects on biological systems.

"Communication System" as used herein, may refer to a wireless communication device that can be configured to transmit and receive information from a processor to a receiver in a smart hand held electronic device.

"Digital Element" as used herein, may refer to electronic components on a substrate. "Smart Hand held Device" as used herein, may refer to a smartphone or tablet built on a mobile operating system and having advanced processing capabilities.

"Feminine Hygiene Product" as used herein refers to but is not limited to a tampon, sanitary pad, panty liner, or other product used to absorb or contain menstruation or bodily fluid discharge.

"Hygiene Product" as used herein refers to any absorbent material or device used by adults to absorb or contain bodily fluid discharge, including but not limited to tampons, liners, men's guards and shields, adult diapers and booster pads.

"Microfluidic Analytical Systems" as used herein may refer to a low energy consumption system including one or more pore(s) from which a fluid sample may be collected, and in some embodiments, moved through a channel or diffused, for the characterization of one or more properties of the fluid sample. In some embodiments, the microfluidic analytical systems can include microfluidic components, such as micro-pumps and micro-valves.

"Power Source" as used herein refers to any device or layer which is capable of supplying energy or placing a logical or electrical device in an energized state. The power source may include batteries. The batteries can be formed from alkaline cell chemistry and may be solid-state batteries or wet cell batteries.

"Sensor Array" as used herein means a sensor or a plurality of sensors, which may include, for example, resistive or capacitive to detect liquid or moisture.

Figure 1:
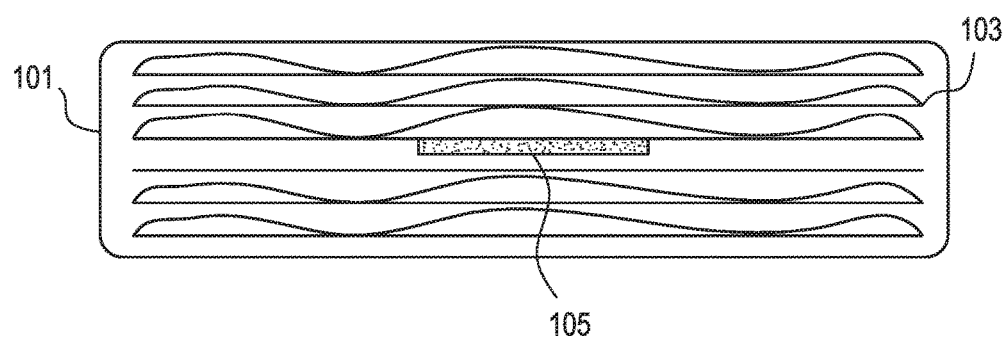
FIG. 1 illustrates an embodiment of a cross-section of a personal hygiene product with digital element embedded within the absorbent materials of the product in accordance with the present invention.

"Switch" as used herein means a circuit element that controls the flow of electrical current in response to a physical or electrical input Personal Hygiene Product Referring now to FIG. 1, a cross section of an embodiment of a personal hygiene product 101 with a digital element 105 is illustrated. The digital element 105 is embedded in the absorbent core 103 of the personal hygiene product that is inserted into or placed against a user's body. In some embodiments, the digital element 105 is located on the body-side exterior surface of a personal hygiene product that is inserted into or placed against a user's body. In some embodiments, the digital element 105 comprises a substrate, comprising, for example, a biocompatible polymer or other flexible, biocompatible material, incorporated with electronic components for power, sensing, and communication.

Figure 2A:
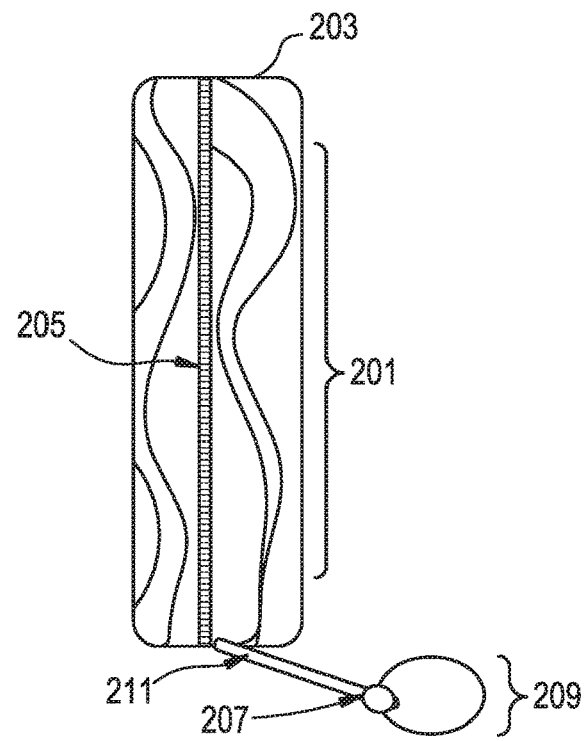
FIGS. 2A and 2B illustrate an embodiment of a cross-section of a personal hygiene product with digital element magnetically connected externally to the personal hygiene product with a conductive ribbon within the absorbent materials of the product in accordance with the present invention.
Figure 2B:
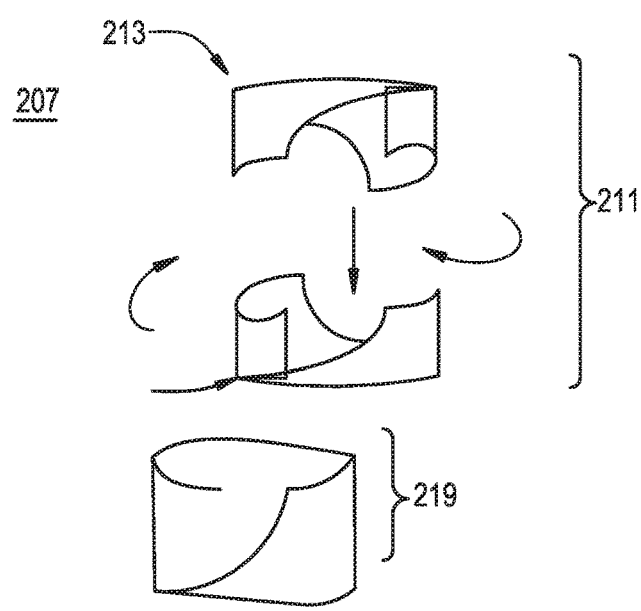

Referring now to FIG. 2, a cross section of a personal hygiene product 201 with an external digital element 209 is comprised of a sensor assembly 205, comprising, for example, a sensor array, running through the center of the absorbent core 203 of the personal hygiene product 201 with an external digital element 209. The sensor array 205 may be, for example, comprised of metalized fiber of ribbons or may be comprised of conductive ink utilized in the thread within the hygiene product. In some embodiments, the conductive ink may be printed on a substrate within the personal hygiene product 201. The sensor array 205 may be capable of sensing conductive and ionic properties bodily fluids absorbed by personal hygiene product 201. The sensor array 205 may capture resistive change in the hygiene product as it becomes saturated with bodily fluids. The sensor array 205 is electrically coupled to external digital element 209 via signal transmission conduit 211. In some embodiments, signal transmission conduit 211 may be magnetically connected to digital element 209. For example, signal transmission conduit 211 may include a magnetic coupling 213 on a first end and digital element 209 may include a mating magnetic coupling 215, which, when joined, form secure coupling 207.

Digital Element

Figure 3:
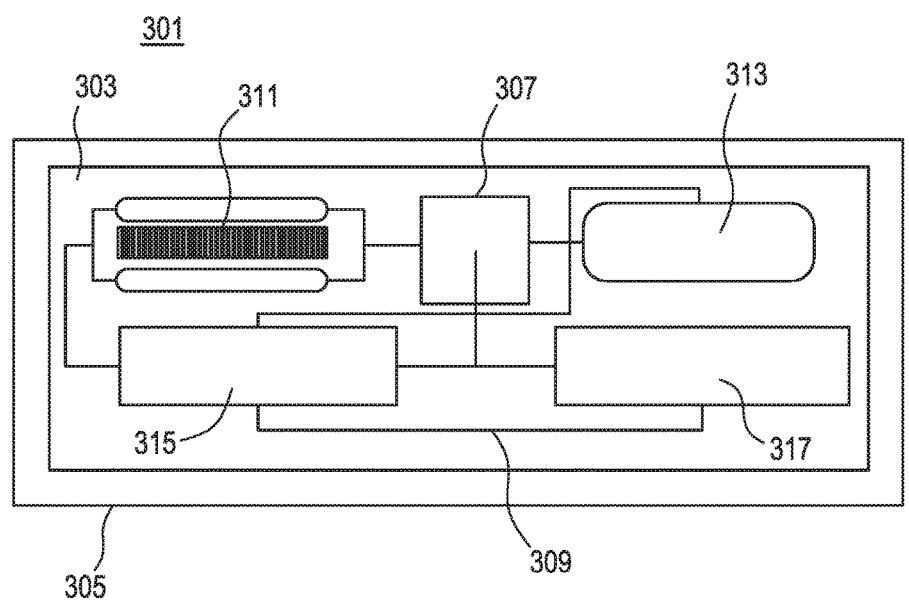
FIG. 3 illustrates a top down view of an embodiment of the digital element comprised of a substrate embedded within the absorbent layers of the personal hygiene product in accordance with the present invention.

In FIG. 3, an embodiment of a digital element 301 is illustrated. In some embodiments, the substrate 303 is encased or encapsulated within a biocompatible polymer layer 305. In some embodiments, a power source 307, which may be, for example, an activation element or a battery, is attached to the substrate 303. The substrate 303 may be comprised of, for example, polyimide, cellulose nanofibrillated fiber, or other biocompatible polymer or silicon. In some embodiments, conductive traces 309 may electrically interconnect the power source 307 with the electronic components 311, 313, 315, and 317 collectively.

In some embodiments, the electronic components may include a sensor array 311 that comprises a single sensor attached to the power source 307 and a processor 315 capable of data collection. The sensor or sensor array may, for example, include an optical sensor, an oximetry sensor, an electrical sensor, a chemical sensor, a mechanical sensor, a MEMS sensor, a nanosensor, a biochemical sensor, an acoustic sensor, an immunologic sensor, a fluidic sensor, or a "lab on a chip" type sensor.

In some embodiments, the electronic components may include a sensor array 311 attached to the power source 307 and a processor 315. In some embodiments, the first processor 315 that collects data from the sensor array 311 communicates with a second processor 317 that is capable of wireless communication with a smart hand held electronic device, which may be, for example, a smartphone or tablet. Processors 315 and 317 are preferably implemented in a single microprocessor.

In some embodiments, the electronic components may include a microfluidic analytical system 313 attached to a power source 307 that communicates with a first processor 315 that collects data. In some embodiments, the first processor 315 communicates with a second processor 317 capable of wireless communication with a smart hand held electronic device, which may be, for example, a smartphone or tablet.

In some embodiments, the electronic components may include a sensor array 311 that may capture data regarding the liquid absorption capacity and saturation level of the personal hygiene product and communicate that data to a processor 315. In some embodiments, the sensor array may capture data regarding the absorption capacity of the personal hygiene product and communicate that data to a processor 315. A first processor 315 may aggregate the collected data generated by the sensor array 311 and transmit the collected data to the second processor 317 that may wirelessly communicate the collected data to a smart hand held electronic device.

In some embodiments, the electronic components may include a sensor array 311 that may capture biometric data, including but not limited to, for example, temperature of the body, pH level, blood oxygen saturation, blood glucose levels, chemical composition, hormone levels, and body motion, and communicate that data to a processor 315. A first processor 315 may aggregate the collected data generated by the microfluidic analytical system 313 and transmit the collected data to the second processor 317 that may wirelessly communicate the collected data to a smart hand held electronic device by, for example, low power blue tooth wireless communication or near field wireless communication.

In some embodiments, the electronic components may include a microfluidic analytical system 313 that may capture data regarding biometrics, including but not limited to, for example, the presence of harmful bacteria, hormone levels, cervical and uterine health indicators, or any cancerous markers, and communicate that data to a processor 315. A first processor 315 may aggregate the collected data generated by the microfluidic analytical system 313 and transmit the data to the first processor 315 and then to processor 317 that may wirelessly communicate the collected data to a smart hand held electronic device.

Figure 4:
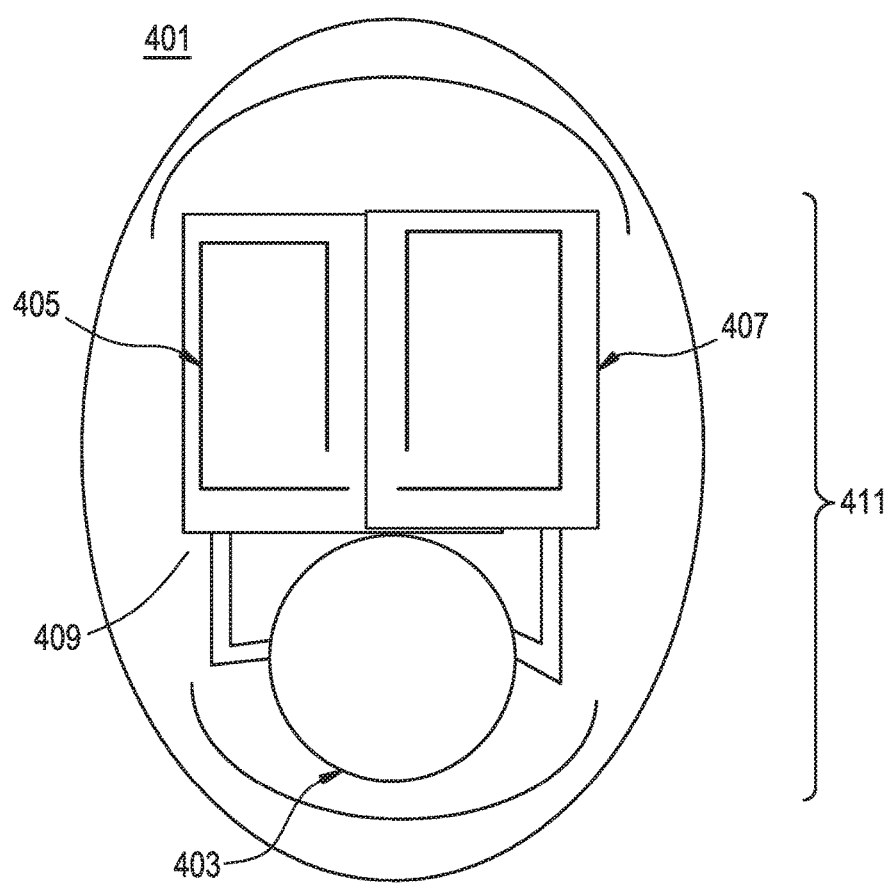
FIG. 4 illustrates a top down view of an embodiment of the digital element comprised of an external substrate that connects to a conductive ribbon within the absorbent materials of the product in accordance with the present invention.

Referring now to FIG. 4, an embodiment of a reusable external digital element 401 is illustrated. The digital element attaches to the sensor array in the personal hygiene product by interlocking magnetic connection, such as that described above in connection with FIG. 2. The digital element 401 may be comprised of a substrate 409 with electronic components 411. The substrate 403 may be comprised of, for example, polyimide, cellulose nanofibrillated fiber, or other biocompatible polymer. The digital element 401 may be encapsulated in a biocompatible material, for example, silicone. The electronic components 411 may be comprised of a communication circuit 405, processor circuit 407, and a power source 403. The communication circuit 405 and processor circuit 407 may be, for example, a flexible or rigid thin printed circuit board. The communication circuit board 405 may facilitate wireless communication with a smart hand held device by, for example, low power blue tooth or near field communication. The communication circuit board 405 may include an antenna comprised of, for example, graphene or a bioabsorbable or biologically inert conductive ink. The processor circuit board 407 may include a sensor array capable of processing data generated by the user's wear of the personal hygiene product. The power source 403 may be, for example, a battery, fuel cell or any other power source suitable for powering microelectronic components. Such suitable devices include, but are not limited to, lithium manganese dioxide coin cells.

Smart Hand Held Device

Figure 5:
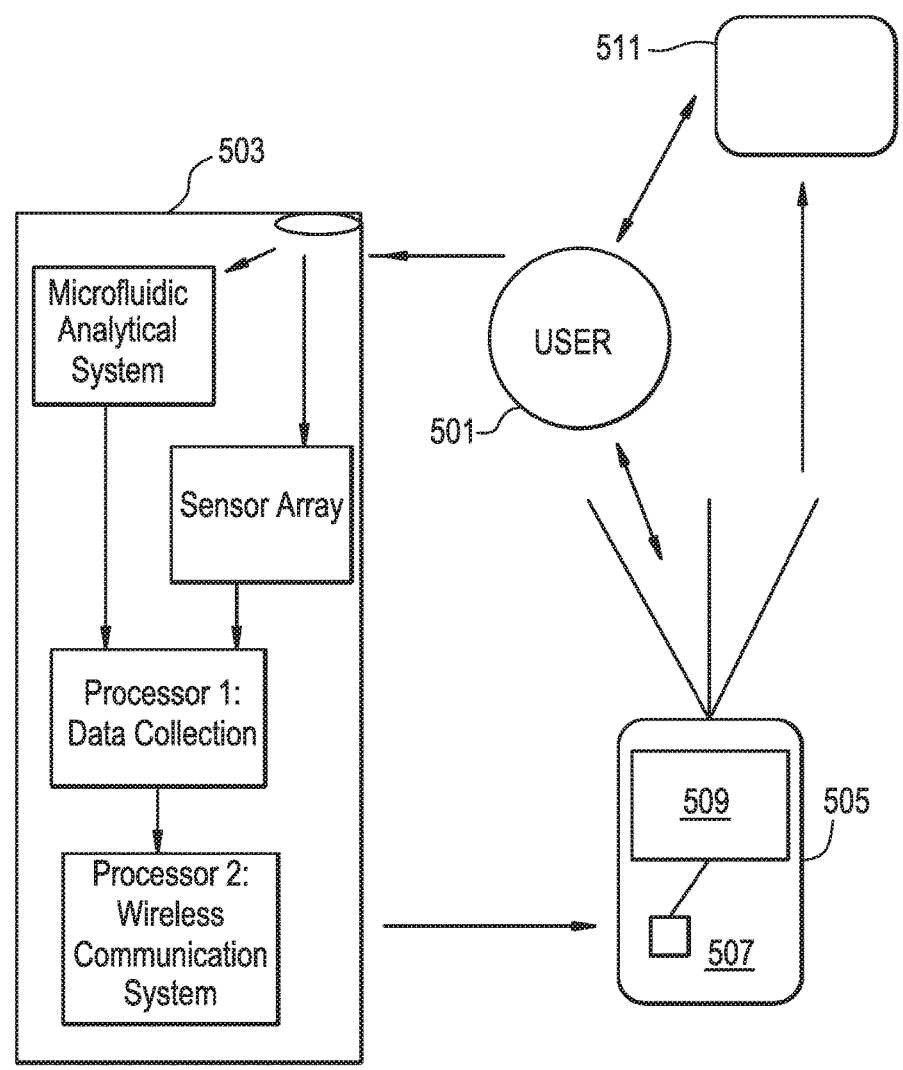
FIG. 5 illustrates a diagrammatic representation of the personal hygiene product with digital element detection path utilized to detect user data and wirelessly communicate that data to a smart hand held electronic device in accordance with the present invention.

Referring now to FIG. 5, a diagrammatic representation of the digital element 503 and the interface with a smart hand held device 505 and the interface of the smart hand held device 505 with a user 501 and/or an internet-based consumer service 511 is illustrated. The smart hand held device 505 may comprise a hand held personal electronic device such as, for example, a cell phone or tablet.

In some embodiments, the digital element 503 is capable of wireless communication with a smart hand held electronic device 505 that has a receiver 507. In some embodiments, the receiver 507 is capable of transmitting user-based data to a processor in the external device that may include, for example, a software application 509 capable of quantifying the user-based data. The user 501 may then interface with the external electronic device 505 and receive in some way the user-based quantified data.

In some embodiments, the software application 509 functions, may include, for example, an interface that quantifies the user-based data received and generates a visual representation of quantified data for the user 501, including but not limited to, for example, generation of a chart, display, or alert for the user 501.

In some embodiments, the software application 509 may be able to provide the user with visual representation of the level of absorption by the personal hygiene product based on liquid absorption capacity and actual body fluid absorption. In some embodiments, the software application 509 may be able to provide the user with time frame for absorbency and anticipated saturation points. In some embodiments, the software application 509 may generate an alert signal to the user if saturation of the personal hygiene product is impending or reached. In some embodiments, the software application 509 may generate a visual representation of the quantified data, including but not limited to, for example, the user's rate of bodily fluid discharge or historical data of bodily fluid discharge.

In some embodiments, the software application 509 may be capable of accumulating data generated over time from use of multiple personal hygiene products. In some embodiments, the software application 509 may be able to generate a graphic, chart, or other interface to illustrate a baseline for the body fluid discharge based on the historical data. In some embodiments, the software application 509 may be able to generate predictive analytics and communicate that information to a user. Such information may allow the user 501 to anticipate start and end dates, for example, if the personal hygiene product with a digital element is used for a menstruation cycle. Such information may allow the user 501 to understand the course of a cycle, including days or time periods of heavier or lighter flow.

In some embodiments, a software application 509 may generate information on a consumable usage rate for the user, predicting how many personal hygiene products are needed, including but not limited to, for example, per day, per week, or per cycle. In some embodiments, a software application 509 may generate a reminder or warning for a user to purchase personal hygiene products, including but not limited to, for example, where a start date for menstruation has been identified. In some embodiments, a software application may provide the user an order quantity estimation based on historical data of the user's bodily fluid discharge. In some embodiments, the interface of the software application 509 may provide a direct link to an internet-based consumer service where a user 501 may order and purchase additional personal hygiene products for direct delivery. In some embodiments, the software application 509 may be capable of automatic direct order placement based on consumable usage rate for delivery direct to user 501. The software application 509 may facilitate purchase of additional personal hygiene products. The software application 509 may connect the user to internet-based consumer services.

Tampon

In accordance with one embodiment of the invention, a personal hygiene product 701 in the form of a tampon with a digital element is provided. Referring to FIG. 7, personal hygiene product 701 is coupled to an external digital element 709 via a signal transmission conduit 706. Disposed within personal hygiene product 701 is a conductive sensor assembly (not shown), for example, running through the center of the absorbent core 703 of the personal hygiene product 701.

Figure 8:
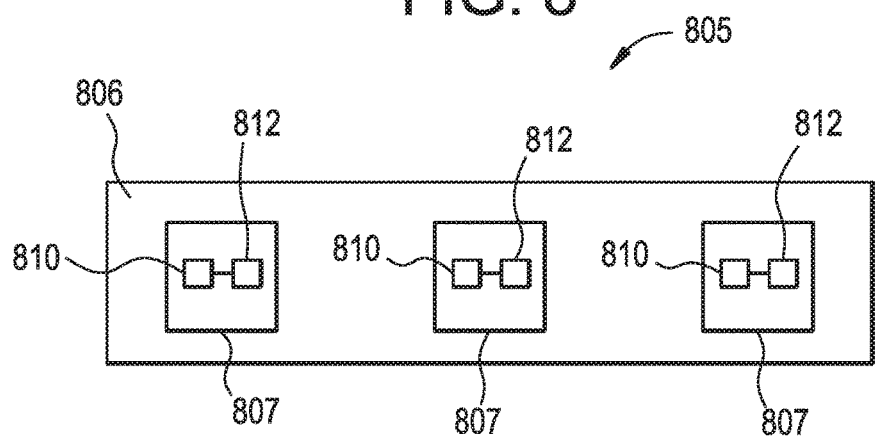
FIG. 8 depicts a sensor array in accordance with an embodiment of the invention.

In at least one embodiment, as illustrated in FIG. 8, conductive sensor assembly 805 generally comprises one or more moisture sensors 807 that may be capable of sensing conductive and ionic properties of menstrual fluid by, for example, measuring resistance. Moisture sensors 807 are disposed on a substrate that may comprise PET, polyimide, cellulose nanofibrillated fiber, or other biocompatible polymer or silicon. In some embodiments, the substrate may comprise a flexible circuit board. Each moisture sensor includes a moisture sensitive switch 810 coupled to a resistor 812. Moisture sensitive switch 810 is configured to conduct or "turn on" when in wetting contact with menstrual fluid and thus generate a signal indicative of the saturation level of the personal hygiene product.

Figure 9:
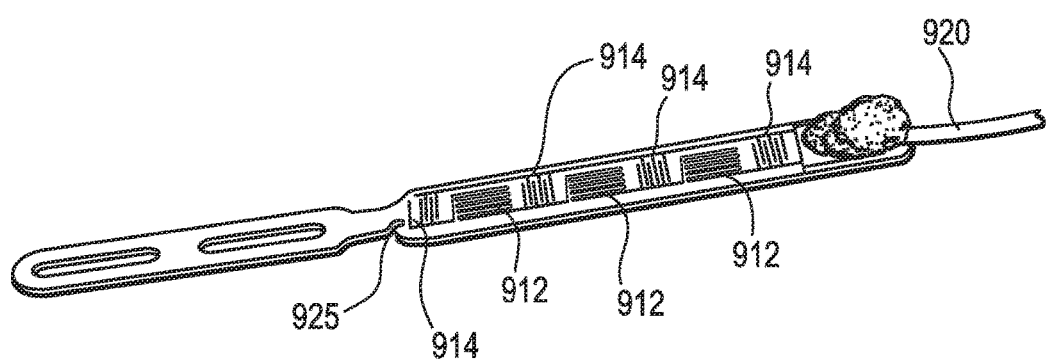
FIG. 9 illustrates a sensor assembly in accordance with the invention.

FIG. 9 illustrates a conductive sensor assembly including resistors 912 connected to moisture sensitive switches in the form of interdigitated electrode patterns 914. The presence of salt and other ionic constituents of the menstrual fluid between and around interdigitated electrodes 914 facilitates conductivity between interdigitated electrodes 914 in the presence of menstrual fluid where there is no statistically significant conductivity between interdigitated electrodes 914 when they are dry. A signal transmission conduit 920 is provided to carry the signal transmitted by the moisture sensitive switches to the digital element. In some embodiments, signal transmission conduit 920 may be a cable connected to a digital element such as that described above in connection with FIG. 4. In some embodiments, transmission conduit 920 may comprise conductive ink deposited on a flexible substrate. Resistors 912 may be formed from conductive ink deposited on substrate 925. In some embodiments, where substrate 925 is a flexible circuit board, resistors 912 may be on board resistors.

It is believed that the constituents of menstrual fluid vary widely from subject to subject. Accordingly, conductivity of menstrual fluid may well vary by as ±50% or more from subject to subject due at least in part to differing ionic content as well as other factors. This conductivity inconsistency across subjects may cause moisture sensors to behave differently for different subjects. For example, due to the differences in menstrual fluid conductivity, a moisture sensor may indicate that a personal hygiene product used by a first subject is saturated and fail to indicate that a personal hygiene product used by a second subject is saturated when both personal hyigiene products are exposed to identical amounts of menstrual fluid. In order to provide more consistent results from subject to subject, in some embodiments resistance values for resistors 812 and moisture sensitive switches 810 are selected so as to minimize the impact of menstrual fluid conductivity variation. Accordingly, the resistance of resistors 812 is preferably much greater than the resistance of moisture sensitive switches 810. In some embodiments resistors 812 may have a resistance value between 1kΩ and 10kΩ. However, these resistance values can be tuned to cause the personal hygiene product to behave in a specifically desired manner.

In some embodiments, conductive sensor assembly 805 may extend generally the entire axial length of the tampon so as to detect saturation at various points along the axial length of tampon. In some embodiments, conductive sensor assembly may include only a single moisture sensor positioned at point along the tampon which indicates full saturation of the tampon. In other embodiments, moisture sensors may be positioned at various points along the axial length of the tampon, e.g., 10%, 50%, 75% and 90%.

Operation

Figure 6A:
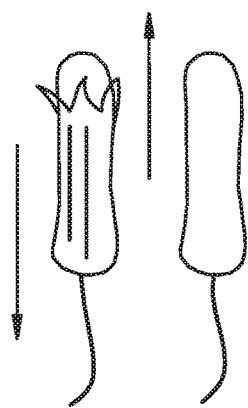
FIGS. 6A-6C illustrate embodiments of activating the digital element prior to use in accordance with the present invention.
Figure 6B:
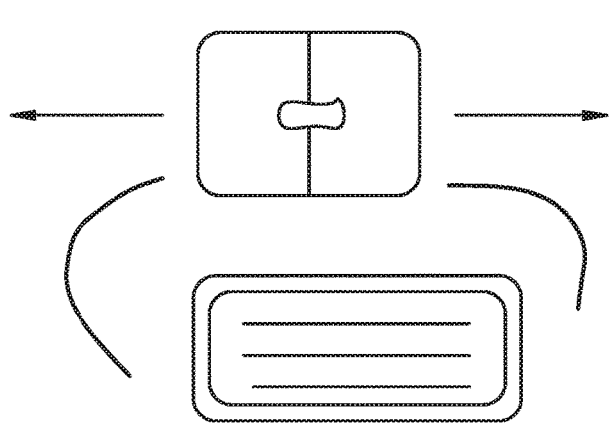
Figure 6C:
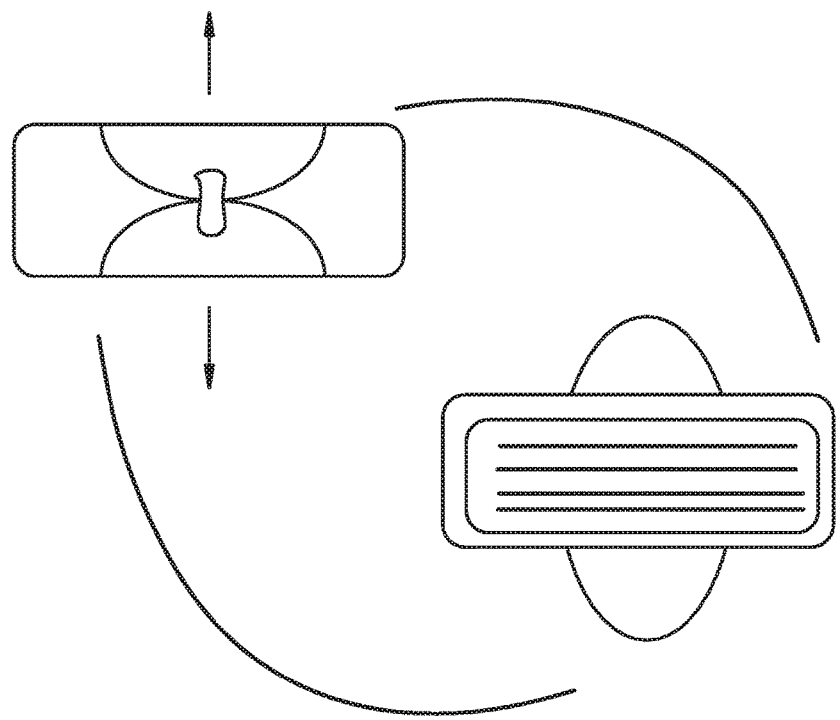

Referring now to FIG. 6, a diagrammatic representation of the activation of the digital element in the personal hygiene product is illustrated. In operation, a user may use the personal hygiene product in a manner consistent with industry use, including but not limited to, for example, insertion into the body 6A, placement directly against the body 6B, or adhesion to an undergarment and placement directly against the body 6C. The user may, prior to placement or insertion of the product near or in the body, activate the digital element by unfolding or pushing the product through an applicator (FIGS. 6A, 6B, and 6C). When the digital element has been activated, the user may then place or insert the personal hygiene product.

A personal hygiene product with a digital element can be, for example, in the form of a tampon, sanitary napkin, panty liner, and diaper, and the like. Specific examples have been described to illustrate embodiments of the device. These examples are for said illustration and are not intended to limit the scope of the claims in any manner. Accordingly, the description is intended to embrace all embodiments that may be apparent to those skilled in the art.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A personal hygiene product with a digital element comprising:
    a personal hygiene product having an axial length comprising an absorbent core in a form suitable for insertion into a user's body to absorb menstrual fluid;
    a conductive sensor assembly disposed within the absorbent core including one or more moisture sensors disposed on a sensor substrate, each moisture sensor being located at a select position along the axial length of said personal hygiene product, each moisture sensor including a moisture sensitive switch connected to a resistor where a resistance value of the moisture sensitive switch is less than a resistance value of the resistor and wherein each resistor is between 1 kΩ and 10 kΩ, said conductive sensor assembly generating a signal indicative of saturation level of said personal hygiene product when said conductive sensor assembly is in wetting contact with the menstrual fluid;
    an external digital element coupled to said conductive sensor assembly including a substrate having a communication circuit capable of wireless communication with a smart hand held electronic device, a processor, a power source and a first mating connector;
    a signal transmission conduit extending from said conductive sensor assembly and interconnecting said conductive sensor assembly to said external digital element.

2. The personal hygiene product with a digital element of claim 1 wherein said conductive sensor assembly extends substantially the entire axial length of said personal hygiene product.

3. The personal hygiene product with a digital element of claim 1 wherein the one or more moisture sensitive switches include an interdigitated electrode structure connected to a resistor.

4. The personal hygiene product with a digital element of claim 1 further wherein said signal transmission conduit includes a magnetic connector and said external digital element includes a mating magnetic connector such that said external digital element is magnetically connected to said signal transmission conduit.

5. The personal hygiene product with a digital element of claim 1 wherein the conductive sensor assembly is capable of sensing biometric data of the user.

6. The personal hygiene product with a digital element of claim 1 wherein the conductive sensor assembly is capable of sensing pH level of the bodily fluid discharge of a user and surrounding environment.

7. The personal hygiene product with a digital element of claim 1 wherein the conductive sensor assembly is capable of sensing temperature of the user.

8. The personal hygiene product with a digital element of claim 1 wherein the conductive sensor assembly is capable of sensing hormone levels.

9. The personal hygiene product with a digital element of claim 1 wherein the communication circuit is capable of low power blue tooth wireless communication with a smart hand held device.

10. The personal hygiene product with a digital element of claim 1 wherein the communication circuit is capable of near field wireless communication with a smart hand held device.

11. The personal hygiene product of claim 1 wherein the smart hand held device comprises a hand held personal electronic device capable of interface with a user.

12. The personal hygiene product with a digital element of claim 11 wherein the smart hand held device includes a receiver and a software application.

13. The personal hygiene product with a digital element of claim 11 wherein the smart hand held device includes a software application capable of signaling or alerting a user-based quantified data received from said conductive sensor assembly.

14. The personal hygiene product with a digital element of claim 11 wherein the smart hand held device includes a software application capable of direct order and purchase of additional personal hygiene products through an internet-based consumer services.

15. The personal hygiene product with a digital element of claim 11 wherein the smart hand held device includes a software application capable of estimating order quantity based on historical data of bodily fluid discharge.

16. The personal hygiene product with a digital element of claim 11 wherein the smart hand held device includes a software application capable of predicting time and rate of bodily fluid discharge.

17. The personal hygiene product with a digital element of claim 1 wherein said signal transmission conduit includes a cable.

18. The personal hygiene product with a digital element of claim 1 wherein said signal transmission conduit includes conductive ink deposited on a flexible substrate.

19. The personal hygiene product with a digital element of claim 1 wherein said signal transmission conduit is magnetically coupled to said digital element.

\* \* \* \* \*